United States Patent
Lautt et al.

(10) Patent No.: US 7,622,447 B2
(45) Date of Patent: Nov. 24, 2009

(54) USE OF GLUTATHIONE SYNTHESIS STIMULATING COMPOUNDS IN REDUCING INSULIN RESISTANCE

(75) Inventors: W. Wayne Lautt, Winnipeg (CA); Paula Macedo, Caxias (PT)

(73) Assignee: DiaMedica Inc., Winnipeg (CA)

( * ) Notice: Subject to any disclaimer, the term of this patent is extended or adjusted under 35 U.S.C. 154(b) by 0 days.

(21) Appl. No.: 10/502,065

(22) PCT Filed: Jan. 27, 2003

(86) PCT No.: PCT/CA03/00079

§ 371 (c)(1), (2), (4) Date: Jan. 18, 2005

(87) PCT Pub. No.: WO03/061639

PCT Pub. Date: Jul. 31, 2003

(65) Prior Publication Data

US 2005/0124552 A1    Jun. 9, 2005

Related U.S. Application Data

(60) Provisional application No. 60/350,955, filed on Jan. 25, 2002.

(51) Int. Cl.
*A61K 38/06* (2006.01)
*C01B 21/24* (2006.01)

(52) U.S. Cl. .................. 514/18; 530/331; 423/405; 435/370

(58) Field of Classification Search .............. None
See application file for complete search history.

(56) References Cited

U.S. PATENT DOCUMENTS 6,436,996 B1 * 8/2002 Vitek et al. .............. 514/565

FOREIGN PATENT DOCUMENTS

| WO | WO 92/18002 | 10/1992 |
|----|----|----|
| WO | WO 00/07575 | 2/2000 |
| WO | WO 00/19992 | * 4/2000 |
| WO | WO-00/19992 | * 4/2000 |

OTHER PUBLICATIONS

Stoyanovsky, et al., Cell Calcium, 1997, 21(1), 19-29.*
[Retrived from]http://dictionary.cambridge.org/results.asp?dict=A &searchword=of, 2007, 1 page [retrived on Jul. 11, 2007].*
Mattia, et al., Diabetologia, 1998, 41, 1392-1396.*
Buckley, 2000, Am. J. Physiol. Cell Physiol, 279, C1168-C1176.*
Corrales, 1999, Journal of Hepatology, 31, 887-894.*
Mattia, 1998, Diabetooglia, 41, 1392-1396.*
Kondo, 1997, FEBS Letters, 413, 236-238.*
Mattia, 1998, Diabetologia, 41, 1392-1396.*
Robak, 1995, Pol. J. Pharmacol., 47, 63-67.*
Guarino et al., 2003, "Hepatic glutathione and nitric oxide are critical for hepatic insulin-sensitizing substance action," *Am. J. Physiol Gastrointest Liver Physiol*, vol. 284, pp. G588-G594.
Anderson, 1998, "Glutathione: an overview of biosynthesis and modulation," *Chemico-Biological Interactions* 111-112, pp. 1-14.
File History for US 6,436,996, 2002.
Czech et al., (1978) "Insulin Response in Skeletal Muscle and Fat Cells of the Genetically Obese Zucker Rat", *Metabolism*, Vo. 27, No. 12, Suppl. 2 (Dec.) pp. 1967-1981.
De Mattia et al., (1998) "Influence of Reduced Glutathione Infusion of Glucose Metabolism in Patients With Non-Insulin-Dependent Diabetes Mellitus", *Metabolism*, Vo. 47, No. 8 (Aug.) pp. 993-997.
Dowell et al., (1999) "Decreased basal despite enhanced agonist-stimulated effects of nitric oxide in 12-week-old stroke-prone spontaneously hypertensive rate", *European Journal of Pharmacology*, 379: 175-182.
Khamaisi et al., (2000) "Effect of inhibition of glutathione synthesis on insulin action: in vivo and in vitro studies using buthionine sulfoximine", *Biochem. J.*, 349: 579-586.
Khamaisi et al., (1997) "Lipoic Acid Reduces Glycemia and Increases Muscle GLUT4 Content in Streptozotocin-Diabetic Rats", *Metabolism*, Vo. 46, No. 7 (Jul.): pp. 763-768.
Lautt et al., (1998) "Rapid insulin sensitivity test (RIST)", *Can. J. Physiol. Pharmacol.*, 76: 1080-1086.
Lautt (1999) "The HISS story overview: a novel hepatic neurohumoral regulation of peripheral insulin sensitivity in health and diabetics" *Can. J. Physiol. Pharmacol.*, 77: 553-562.
Marinho et al., (1997) "Glutathione metabolism in hepatomous liver of rats treated with diethylnitrosamine", *Biochimica et Biophysica Acta*, 1360: 157-158.
Modan et al., (1985) "Hyperinsulinemia", *J. Clin. Invest.*, vol. 75, pp. 809-817.

(Continued)

*Primary Examiner*—Andrew D Kosar
*Assistant Examiner*—Satyanarayana R Gudibande
(74) *Attorney, Agent, or Firm*—Brian R. Dorn; Merchant & Gould P.C.

(57) ABSTRACT

There is provided a method of reducing insulin resistance in a mammalian patient comprising selecting a patient suffering from insulin resistance and administering a compound which increases hepatic glutathione and a compound which increases hepatic nitric oxide.

13 Claims, 5 Drawing Sheets

OTHER PUBLICATIONS

Petrie et al., (1996) "Endothelial Nitric Oxide Production and Insulin Sensitivity", *Circulation*, 93: 1331-1333.

Rett et al, (1996) "Alpha-Liponsaäure (Thioctsäure) steïgert die Insulinempfindlichkeit übergewichtiger Patienten mit Typ-II-Diabetes", *Diabetes Und Soffwechsel* 5, Supplement-Heft 3: 59-63.

Sadri et al., (1999) "Blockade of hepatic nitric oxide synthase causes insulin resistance", *Am. J. Physiol.* 277: G101-G108.

Schrammel et l., (1998) "Activation of Soluble Guanylyl Cyclase by the Nitrovasodilator 3-Morpholinosydnonimine Involves Formation of S-Nitrosoglutathione", *Molecular Pharmacology*, 54: 207-212.

Wang et al., (1998) "Evidence of nitric oxide, a flow-dependent factor, being a trigger of liver regeneration in rats", *Can. J. Physiol. Pharmacol.* 76: 1072-1079.

Xie et al., (1996) "Insulin resistance of sketetal muscle produced by hepatic parasympathetic interruption", *Am. J. Physiol.*, 270: E858-E863.

Young et al. (1998) "Evidence for altered sensitivity of the nitric oxide/cGMP signalling cascade in insulin-resistant skeletal muscle", *Biochem. J.*, 329: 73-79.

\* cited by examiner

Control Group (n=6): L-NAME (1mg/kg, ipv) reduces the RIST Index from 260.2 ± 15.6 mg glucose /kg to 121.2 ± 12.8 mg glucose /kg (52.3±5.8% inhibition). SIN-1(5mg/kg, ipv) restores insulin response with a RIST index of 258.1 ±18.5 mg glucose /kg. *** = $p<0.001$

Figure 2(b)

BSO Group (n=5): The control RIST index was 158.4± 12.2 mg glucose /kg. Intraportal administration of L-NAME(1mg/kg) reduced significantly the RIST Index to 109.8± 9.1mg glucose /kg.Ipv administration of SIN-1 did not reverse the RIST Index to control values.
*= p<0.05; ns= non significant

Figure 2(c)

HISS-dependent and HISS-independent components of insulin action in BSO and control groups. HISS-independent components are not different in both groups. HISS is significantly reduced in BSO group (49.3 ±8.56 mg glucose /kg) compared to control group (138.9 ± 22.8 mg glucose /kg) corresponding to a decrease of 64.4% of HISS action. **=$p<0.01$; ns= non significant

Figure 2(d)

USE OF GLUTATHIONE SYNTHESIS STIMULATING COMPOUNDS IN REDUCING INSULIN RESISTANCE

This application is a national stage entry under 35 U.S.C. § 371 of PCT/CA03/00079, filed Jan. 27, 2003, which claims the benefit under 35 U.S.C. § 119(e) of U.S. Provisional Patent Application Ser. No. 60/350,955, filed Jan. 25, 2002, the entire disclosures of which are hereby incorporated by reference.

FIELD OF THE INVENTION

The invention relates to the field of treatments for insulin resistance.

BACKGROUND

Insulin resistance is a significant health challenge for a wide range of patients, including those with type II diabetes, metabolic obesity, and various liver conditions.

The picture that is emerging is one of complex multiple interacting systems with reflex parasympathetic effects in the liver capable of causing more than one reaction and of triggering reactions in other organs.

Fasted cats develop insulin resistance immediately following acute denervation of the liver. In such studies, the degree of reduction of response to insulin was maximal after anterior plexus denervation and did not increase further with addition of denervation of the posterior nerve plexus or bilateral vagotomy thus demonstrating that all of the nerves of relevance were in the anterior plexus.

The rapid insulin sensitivity test (RIST) was employed (Lautt et al., Can. J. Physiol. Pharmacol. 76:1080 (1998)) is employed to avoid the complexity of the reaction to hypoglycemia. The RIST involves use of a euglycemic clamp following the administration of insulin and quantitation of the response as the amount of glucose required to be infused over the test period in order to hold arterial blood glucose levels constant. The RIST methodology has been published in detail and has been demonstrated in both cats and rats. It is highly reproducible with up to five consecutive responses being obtainable in cats and four in rats with blood glucose levels returning to control levels between each test. Insulin, glucagon, and catecholamine levels remain unchanged between tests.

Cats show a dose-related development of insulin resistance using atropine (a cholinergic muscarinic receptor antagonist) that was of a similar magnitude to that produced by surgical denervation. The dose of atropine required to produce a full insulin resistance is 3 mg/kg (4 µmol/kg) administered into the portal vein. A similar degree of insulin resistance was achieved with $10^{-7}$ mmol/kg of the $M_1$ muscarinic selective antagonist, pirenzepine, and with $10^{-6}$ µmol/kg of the $M_2$ selective antagonist, methoctramine. Although not conclusive, the data suggest that the response may be mediated by the $M_1$ muscarinic receptor subtype.

Although the liver appeared to be the organ that produced the insulin resistance, it was not clear that the liver was the resistant organ. In order to determine the site of insulin resistance, a further series was done in cats that measured arterial-venous glucose responses across the hindlimbs, extrahepatic splanchnic organs, and liver. The intestine was unresponsive to the bolus insulin administration both before and after atropine or anterior plexus denervation or the combination of both. The hepatic response was also not notably altered whereas the glucose uptake across the hindlimbs, primarily representing skeletal muscle uptake, was decreased following atropine or hepatic parasympathetic denervation. These results indicated that interference with hepatic parasympathetic nerves led to insulin resistance in skeletal muscle.

It was further demonstrated that the same degree of resistance could be produced by pharmacological blockade of parasympathetic nerve function using the muscarinic receptor antagonist, atropine. Following a meal, insulin is released from the pancreas. The presence of insulin in the blood elicits a hepatic parasympathetic reflex that results in the release of acetylcholine in the liver that results in the generation and release of nitric oxide which acts to control the sensitivity of skeletal muscle to insulin through the action of a hormone released from the liver, a hepatic insulin sensitizing substance (HISS) which selectively stimulates glucose uptake and storage as glycogen in tissues including skeletal muscle.

In the absence of HISS, the large muscle mass is highly resistant to insulin and the glucose storage in skeletal muscle is severely reduced. Interruption of any part of the parasympathetic-mediated release of HISS results in insulin resistance. This parasympathetic reflex regulation of HISS release is an important mechanism by which the body regulates responsiveness to insulin and this mechanism is adjusted according to the prandial state, that is, according to how recently there has been an oral consumption of nutrients.

In a fasted condition, HISS release in response to insulin is minimal or absent so that if insulin is released in this situation, there is a minimal metabolic effect. Following a meal, the parasympathetic reflex mechanism is amplified so that HISS release occurs and results in the majority of the ingested glucose stored in skeletal muscle.

The consequence of lack of HISS release is the absence of HISS which results in severe insulin resistance, referred to as HISS-dependent insulin resistance ("HDIR"). In this situation, the pancreas is required to secrete substantially larger amounts of insulin in order that the glucose in the blood is disposed of to prevent hyperglycemia from occurring. If this condition persists, insulin resistance will progress to a state of type 2 diabetes (non-insulin dependent diabetes mellitus) and eventually will lead to a complete exhaustion of the pancreas thus requiring the patient to resort to injections of insulin. Thus, it appears that any condition in which the hepatic parasympathetic reflex is dysfunctional will result in insulin resistance.

It is believed that the insulin resistance that is seen in a variety of conditions (non-insulin dependent diabetes, essential hypertension, obesity, chronic liver disease, fetal alcohol effects, old age, and chronic inflammatory diseases) represents a state of HDIR parasympathetic dysfunction. Lack of HISS would also be anticipated to result in obesity at the early stage of the resultant metabolic disturbance (the obese often become diabetic).

Normally after a meal the liver takes up a small proportion of glucose and releases HISS to stimulate skeletal muscle to take up the majority of the glucose load. In the absence of HISS, the skeletal muscle is unable to take up the majority of glucose thus leaving the liver to compensate. The hepatic glycogen storage capacity is insufficient to handle all of the glucose, with the excess being converted to lipids which are then incorporated into lipoproteins and transported to adipose tissue for storage as fat. Provision of HISS to these individuals would restore the nutrition partitioning so that the nutrients are stored primarily as glycogen in the skeletal muscle rather than as fat in the adipose tissue.

Thus, it is an object of the invention to provide a method of reducing insulin resistance.

SUMMARY OF THE INVENTION

Nitric oxide (NO), GSH and insulin are believed to act within the liver to cause the release of a hepatic insulin sensitizing substance (HISS) into the blood. HISS controls the sensitivity of certain tissues (including skeletal muscle) to insulin. When HISS is present in significant amounts these tissues become more sensitive to insulin and can rapidly take up and store glucose. While the invention is not limited to any particular mechanism, the insulin sensitizing effect of HISS is believed to result when insulin causes HISS release and then HISS action is imposed on skeletal muscle. The direct action of insulin on peripheral tissues is not believed to be directly altered. Similarly, the term HISS-dependant insulin resistance refers to the decreased glucose storage effect produced by insulin as a result of lack of HISS action, not a direct reduction in cellular response to insulin.

In an embodiment of the invention there is provided a method of reducing HISS-dependent insulin resistance in a mammalian patient suffering therefrom comprising administering a glutathione-increasing compound and in some instances a nitric oxide increasing compound.

Acetylcholine infused directly into the portal vein (2.5 µg/kg/min) results in a complete reversal of the insulin resistance induced by surgical denervation. Administration of the same dose of acetylcholine intravenously produces no reversal. Intraportal administration directly targets the liver whereas intravenous infusion bypasses the liver and is not organ selective. This demonstration is extremely important in that the data suggest that the signal from the liver to skeletal muscle is blood-borne.

A small but significant reduction in insulin resistance is observed following the administration of GSH alone. However, this effect is insufficient for many therapeutic purposes and is believed to be HISS-independent. Improved insulin sensitivity is obtained when both NO and GSH are administered.

A role for nitric oxide ("NO") in reducing insulin resistance has been previously reported (Int. Pub. WO 00/19992 of Lautt). However, it has subsequently been discovered that NO alone is insufficient to fully overcome HISS-dependent insulin resistance in patients suffering therefrom and having low levels of hepatic GSH. While NO alone can increase insulin sensitivity in such patients, the effect is not complete and may not be sufficient for therapeutic purposes. As used herein, the phrase "low levels of hepatic GSH" refers to GSH levels lower than 3.5 µmol/g fresh liver when assayed after a 16 to 24 hour fast.

In an embodiment of the invention there is provided use of a glutathione-increasing compound and a nitric oxide increasing compound in reducing HISS-dependent insulin resistance in a mammalian patient suffering therefrom.

In an embodiment of the invention there is provided use of a glutathione-increasing compound and a nitric oxide increasing compound in the manufacture of a medicament useful in the treatment of HISS-dependent insulin resistance.

In an embodiment of the invention there is provided use of a composition comprising a glutathione-increasing compound and a nitric oxide-increasing compound in improving glucose uptake in a patient suffering from insulin resistance.

DETAILED DESCRIPTION OF THE PREFERRED EMBODIMENTS

Surprisingly, it has been learned that the combined action of glutathione and nitric oxide ("NO") play an important role in the production of HISS in the liver. Glutathione, NO and insulin are needed for the release of sufficient active HISS to overcome HISS-dependent insulin resistance ("HDIR").

HISS-dependent insulin resistance refers to the reduced uptake of glucose by HISS-sensitive tissues in the absence of HISS or when HISS levels are insufficient. One example of such reduced uptake is that of skeletal muscle when observed in the presence of insulin but in the absence of a normal hepatic parasympathetic reflex. While administration of GSH alone or NO alone may reduce insulin resistance somewhat in such a situation, the remaining insulin resistance (not treatable with NO or GSH alone) is HDIR and can be treated by the method disclosed herein.

While the invention is not limited to any particular mechanism, it is believed that the administration of a glutathione increasing compound and an NO-increasing compound restores HISS release from the liver and/or restores HISS effect at skeletal muscle and other HISS-sensitive sites of glucose uptake.

Thus, patients suffering from insulin resistance caused by insufficient HISS activity can be treated through the administration of a hepatic glutathione-increasing compound together with a hepatic NO-increasing compound.

It will be apparent, in light of the disclosure herein, that a number of ways of increasing hepatic glutathione and NO are specifically contemplated and fall within the scope of the invention. For example, hepatic glutathione may be increased by increasing the rate of glutathione synthesis in the liver, reducing the rate of glutathione degradation (other than to form HISS) in the liver, or by providing exogenous glutathione in a form which is taken up by the liver cells. By way of non-limiting example, the rate of glutathione synthesis in the liver may in some instances be increased using one or more compounds: (a) which stimulate enzymes involved in glutathione synthesis (but the compounds are not reactants in the reactions producing glutathione); (b) which are reactants in the reaction producing glutathione; or (c) which stimulate the production of one or more subsequent compounds which either stimulate glutathione producing enzymes or are reactants in the reaction producing glutathione. In light of the disclosure herein, one skilled in the art could select a suitable method of increasing hepatic glutathione. Examples of glutathione-increasing compounds include: n-acetylcysteine, cysteine esters, L-2-oxothiazolidine-4-carboxolate ("OTC"), gamma glutamylcysteine and its ethyl ester, glutathione ethyl ester, glutathione isopropyl ester, lipoic acid, cystine, cysteine, methionine, and s-adenosylmethionine.

Similarly, hepatic NO levels can be increased by increasing the rate of NO synthesis in the liver (such as by increasing NO synthase activity), by reducing the rate of NO degradation in the liver (other than to form HISS), or by providing exogenous NO or an exogenous carrier or precursor which is taken up and releases NO in the liver.

NO-increasing compounds include SIN-1 and molsidamine, and nitrosylated forms of: N-acetylcysteine, cysteine esters, L-2-oxothiazolidine4-carboxolate ("OTC"), gamma glutamylcysteine and its ethyl ester, glutathione ethyl ester, glutathione isopropyl ester, lipoic acid, cystine, cysteine, methionine, and s-adenosylmethionine.

When nitrosylated forms of glutathione-increasing compounds are administered, these compounds can perform the role of both a nitric oxide-increasing compound and a glutathione-increasing compound.

S-adenosylmethionine (SAMe) is a major regulator of hepatic glutathione. SAMe administration causes intrahepatic glutathione to be restored to near-normal levels. Thus, SAMe administration (together with an NO-increasing compound) allows HISS production in patients otherwise suffering from insufficient HISS as a result of insufficient hepatic glutathione. Thus, one method of increasing hepatic glutathione is by the administration of SAMe together with an NO-increasing compound. As used herein "SAMe" includes SAMe itself as well as pharmacologically acceptable salts thereof.

SAMe is preferably administered orally at a dose of 0.5 to 25 mg/kg, by intramuscular injection at a dose of 0.2 to 10 mg/kg, or by another route of administration with an equivalent dose.

Peak glutathione levels are typically seen about 3-6 hours after oral administration of SAMe. In one embodiment, SAMe is administered once per day. In some instances the daily oral dose is preferably taken in the morning.

The precise dose of glutathione-increasing compound and NO-increasing compound desirable will be determined by a number of factors which will be apparent to those skilled in the art, in light of the disclosure herein. In particular, the identity of the glutathione-increasing compound and the NO-increasing compound and its mechanism of action (if known), the formulation and route of administration employed, the unstimulated level of HISS production in response to the patient's endogenous glutathione and/or NO levels, the patient's gender, age and weight, as well as the extent of unstimulated hepatic glutathione and/or NO production and the severity of the condition to be treated should be considered. Where it is impractical to conduct the tests necessary to determine the glutathione and/or NO response and/or the other factors such as the extent of hepatic glutathione and/or NO production, the appropriate dose can be determined through the administration of a dose suitable for a majority of patients similar to the subject in respect of those factors which have been assessed, followed by monitoring of the patient to determine if HISS production is increased. Such monitoring may be by any suitable means including, for example, the RIST.

In one embodiment of the invention, a patient suffering from insulin resistance is treated for that condition by the administration of one or more of S-adenosylmethionine, vitamin E, vitamin C and 3-morpholinosyndnonimine and other pharmaceutically acceptable anti-oxidants, together with a NO-increasing compound.

For oral administration, in some instances the components are preferably administered immediately before a meal: SAMe (1 to 20 mg/kg, preferably 6 mg/kg body weight), vitamin E (1 to 20 mg/kg, preferably 6 mg/kg body weight), vitamin C (1 to 20 mg/kg, preferably 7 mg/kg body weight), and 3-morpholinosyndnonimine ("SIN-1") (50 to 400 mg/kg, preferably 150 mg/kg body weight).

In one embodiment of the invention the glutathione-increasing compound is 8-bromo-cGMP. 8-bromo-cGMP for administration to a patient may be in any pharmaceutically acceptable carrier. In some instances intravenous administration at a dose of 0.05 to 1 mg/kg/min infused continuously will be desired. In some instances a dose of 1 to 0.5 mg/kg/min will be desired. Infusion will preferably commence near the time of a meal so that 8-bromo-cGMP levels in the liver will peak when blood glucose levels are elevated above premeal levels. In some instances 8-bromo-cGMP may be continuously administered for 1 to 60 minutes. In some instances administration for 5 to 30 minutes will be desirable. Comparable oral doses may also be employed, although in some instances it may be desirable to administer an oral dose a greater time prior to a meal than the comparable intravenous dose would be administered.

In one embodiment, the NO-increasing compound is SIN-1. SIN-1 administration to a patient may be in any suitable carrier. In some instances, an intravenous dose of between about 1 and 25 mg/kg body weight administered over a 5 minute period to 1 hour will be desired. In some instances a dose of between about 5 and 20 mg/kg body weight will be desired. In some instances a dose of between 8 and 15 mg/kg body weight will be desired. In some instances the period over which the dose is administered will be adjusted to allow hepatic NO levels to rise in parallel to hepatic GSH levels.

Any suitable glutathione-increasing compound and any suitable NO-increasing compound may be employed. A glutathione-increasing or NO-increasing compound will be "suitable" if: (a) at the dose and method of administration to the mammalian patient, it is not acutely toxic, and does not result in chronic toxicity disproportionate to the therapeutic benefit derived from treatment; and (b) at the dose and method of administration to the mammalian patient, including the impact of a suitable dose of the other (GSH or NO) increasing compound, it reduces insulin resistance in the patient.

In one embodiment there is provided a pharmaceutical composition including a hepatic glutathione-increasing compound and a hepatic nitric oxide-increasing compound.

In one embodiment of the invention, the glutathione-increasing compound and NO-increasing compound are preferentially targeted to the liver. Targeting to the liver can be accomplished through the use of any pharmaceutically acceptable liver targeting substance. For example, each compound can be bound to albumin for preferential delivery to liver; alternatively, the compounds may be incorporated into or encapsulated within liposomes which are preferentially targeted to the liver. Compounds can be bound to bile salts which are selectively taken up by the liver. In one embodiment, one or both compounds are administered in a precursor form, and the precursor is selected to be metabolised to the active form by enzymes preferentially found in the liver.

The glutathione-increasing compound may be administered so as to maintain a relatively constant level of the glutathione-increasing compound in the liver at all times. In some instances it will be preferable to administer the glutathione-increasing compound so as to have its concentrations peak when blood glucose is high, such as after a meal, allowing HISS production and glucose uptake at that time. Where toxicity is a concern, it may be desirable to keep glutathione-increasing compound levels low until blood glucose levels become elevated above normal levels. Alternatively, the glutathione-increasing compound may be administered so as to maintain a relatively constant level of HISS in the liver at all times. Alternatively, the glutathione-increasing compound may be administered to have HISS concentrations peak when blood glucose is high, and to remain high for no more than about 4 to 6 hours.

In some instances, it will be desirable to administer a NO-increasing compound and a GSH-increasing compound together with at least one other drug used in the treatment of diabetes, examples of which are listed in Table I.

TABLE I a. Insulin and insulin analogues
b. Type II Diabetes drugs
    i. Sulfonylurea agents
        1. First Generation
            a. Tolbutamide
            b. Acetohexamide
            c. Tolazamide
            d. Chlorpropamide
        2. Second Generation
            a. Glyburide
            b. Glipizide
            c. Glimepiride
    ii. Biguanide agents
        1. metformin
    iii. Alpha-glucosidase inhibitors
        1. Acarbose
        2. Miglitol
    iv. Thiazolidinedione Agents (insulin sensitizers)
        1. Rosiglitazone
        2. Pioglitazone
        3. Troglitazone
    v. Meglitinide Agents
        1. Repaglinide
c. Phosphodiesterase Inhibitors
    i. Anagrelide
    ii. Tadalafil
    iii. Dipyridamole
    iv. Dyphylline
    v. Vardenafil
    vi. Cilostazol
    vii. Milrinone
    viii. Theophylline
    ix. Sildenafil
    x. Caffeine
d. Cholinesterase Inhibitors
    i. Donepezil
    ii. Tacrine
    iii. Edrophonium
    iv. Demecarium
    v. Pyridostigmine
    vi. Phospholine
    vii. Metrifonate
    viii. Neostigmine
    ix. Galanthamine
    x. Zanapezil
e. Cholinergic Agonists
    i. Acetylcholine
    ii. Methacholine
    iii. Bethanechol
    iv. Carbachol
    v. Pilocarpine hydrochloride In one embodiment of the invention there is provided a method of reducing insulin resistance in a mammalian patient having lower than normal hepatic glutathione levels. In this embodiment the method comprises: selecting a patient suffering from insulin resistance, determining if hepatic glutathione levels are lower than normal in the patient, and administering a compound which increases hepatic glutathione.

As used herein, the phrase "lower than normal hepatic glutathione levels" means hepatic glutathione levels lower than those observed in an average healthy individual of the same gender, age, weight, fed-state, and blood sugar level.

The patient is preferably a mammal. In one embodiment the patient is a human. In another embodiment the patient is a domestic animal such as a cat, dog or horse.

EXAMPLES

Summary: GSH depletion was induced in 5 week old Wistar rats using buthionine sulfoximine (BS), 2 mmol/kg bw, i.p. for 20 days. Control rats were injected with an equal volume of saline. Insulin sensitivity was measured using a euglycemic clamp, the Rapid Insulin Sensitivity Test—RIST. In both the saline group (SG) and BSO group (BG) a control RIST followed by a RIST post-L-NAME (1 mg/kg i.p.v.), a NOS competitive antagonist, and a RIST post-SIN-1 (5 mg/kg i.p.v.), a NO donor, were performed. The liver was removed for further determined of hepatic GSH content using the GSH peroxidase-reductase assay. BG showed a reduction of 48.3±6.9% in hepatic GSH content compared to SG. The control RIST, 248.0±15.8 mg glucose/kg for SG, was impaired in the BG (158.4±12.2 mg glucose/kg; p<0.01). After L-NAME the SG RIST was 129.0±1.9 mg glucose/kg and the BG RIST was 109.0±9.1 mg glucose/kg. SIN-1 administration only restored insulin action in the SG (246.0±11.5 mg glucose/kg). HISS action, quantified by subtracting the post L-NAME RIST from the control RIST, was 114.0±15.8 mg glucose/kg for SG and only 49.3±8.6 mg glucose/kg for BG (p<0.01). HISS dependent insulin resistance appears to be related to impaired levels of GSH in the liver, leading to a compromised HISS secretion/release.

SIN-1 is a NO donor. L-NAME and L-NMMA are nitric oxide synthase (NOS) antagonists.

SIN-1 reverses HISS inhibition after NOS blockade.

SIN-1 produces NO and $O_2^{2-}$ simultaneously. Nitrosatin of GSH by $NO/O_2^{2-}$ to produce GSNO is efficient. GSNO is apparently essential for HISS release. Nitroprusside is not able to restore HISS action after NOS blockade.

Example 1

Figure 1:
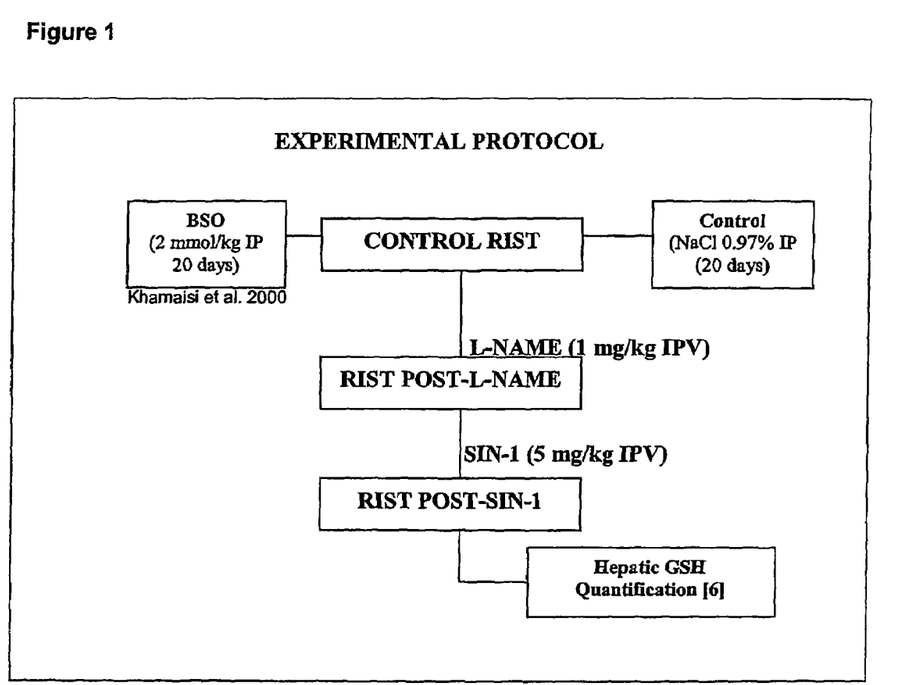
FIG. 1 is a schematic illustration of the experimental protocol employed in Example 1.
Figure 2A:
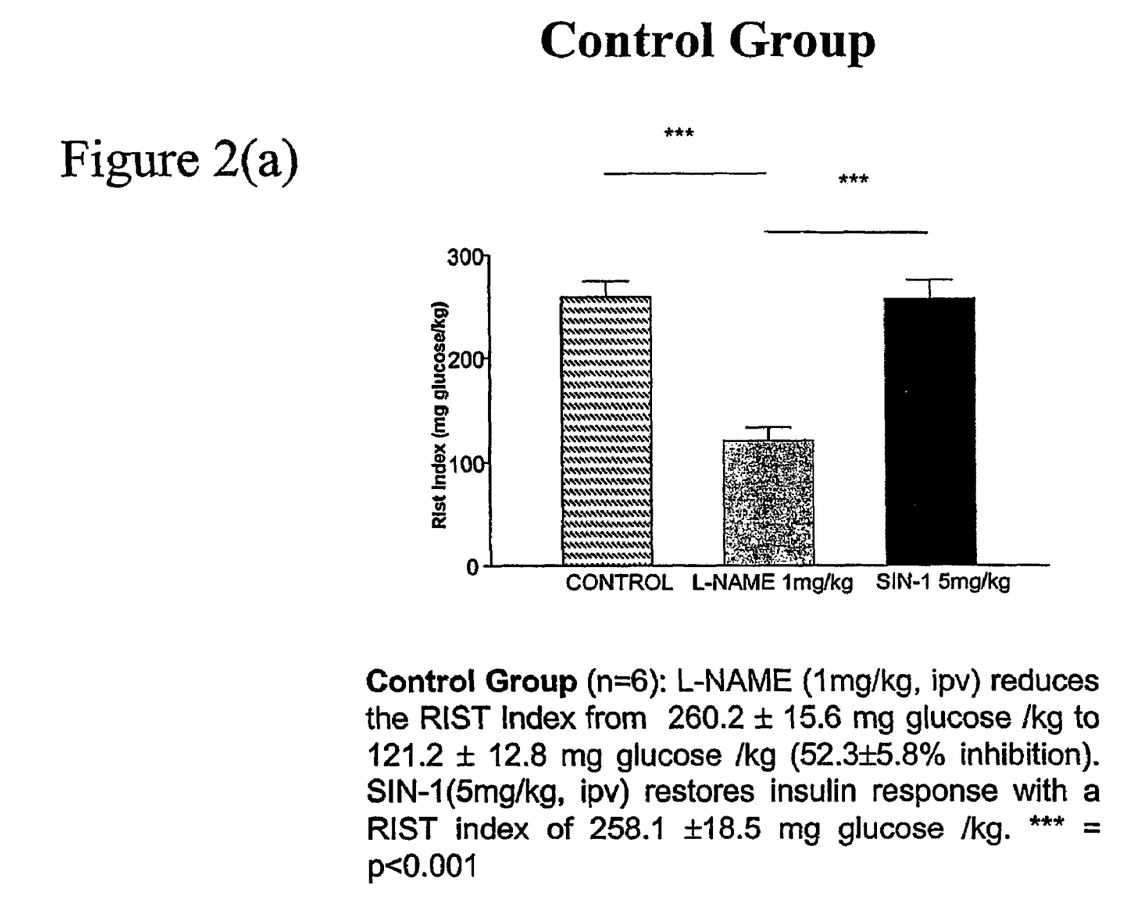
FIGS. 2a-d depict the RIST index for the control group BSO group in Example 1, as well as HISS dependent and independent components of insulin action in the BSO and control groups, and hepatic GSH content in those groups.
Figure 2B:
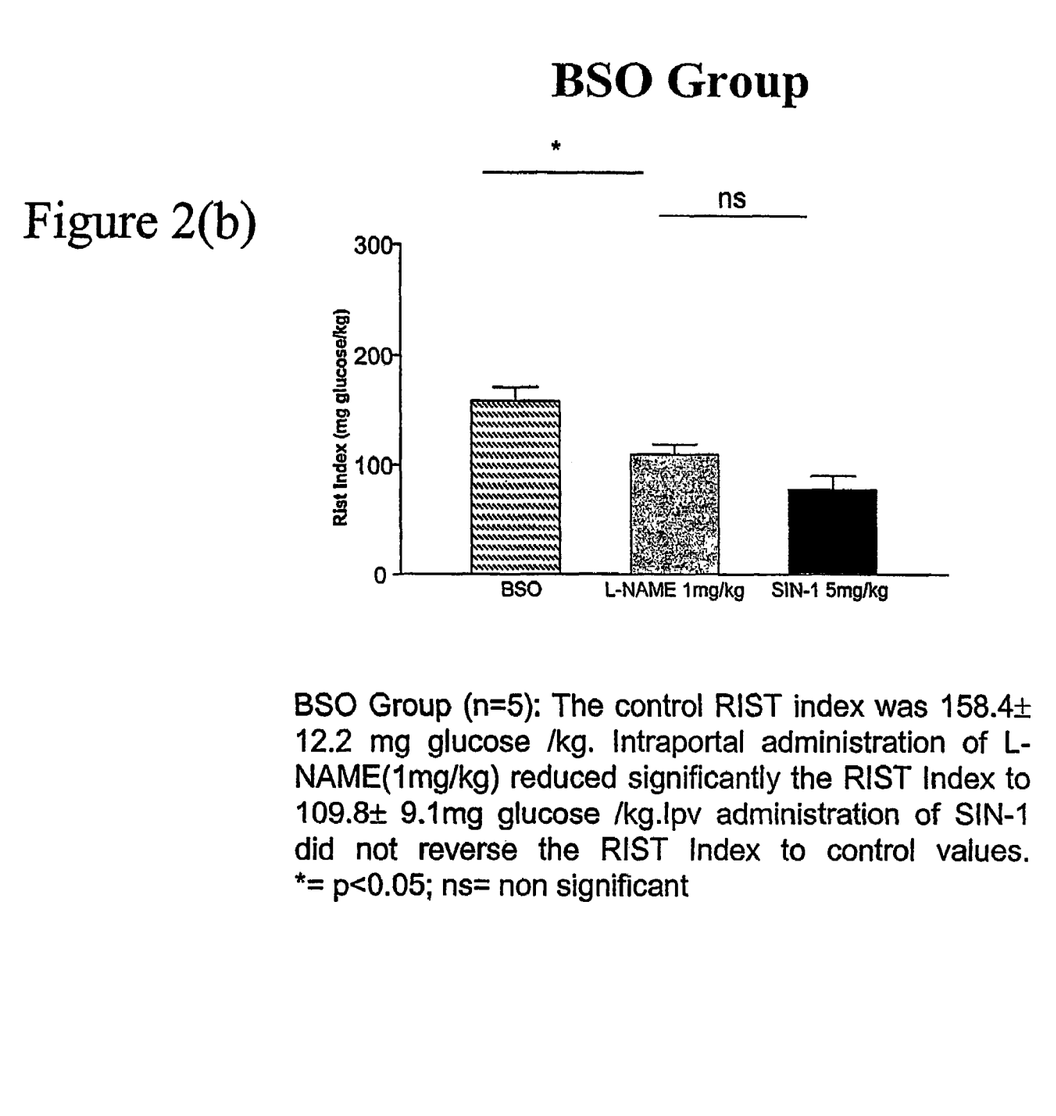
Figure 2C:
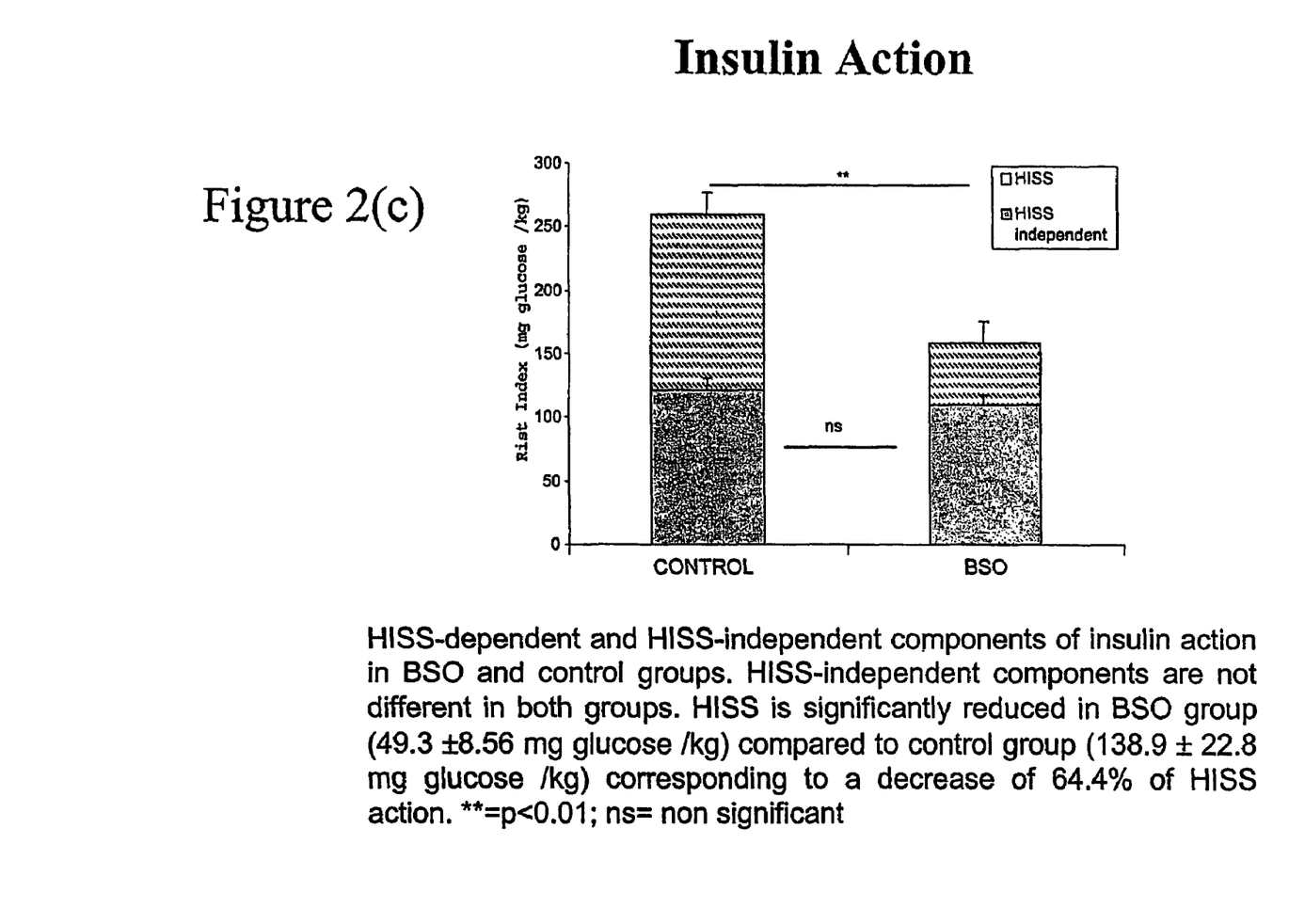
Figure 2D:
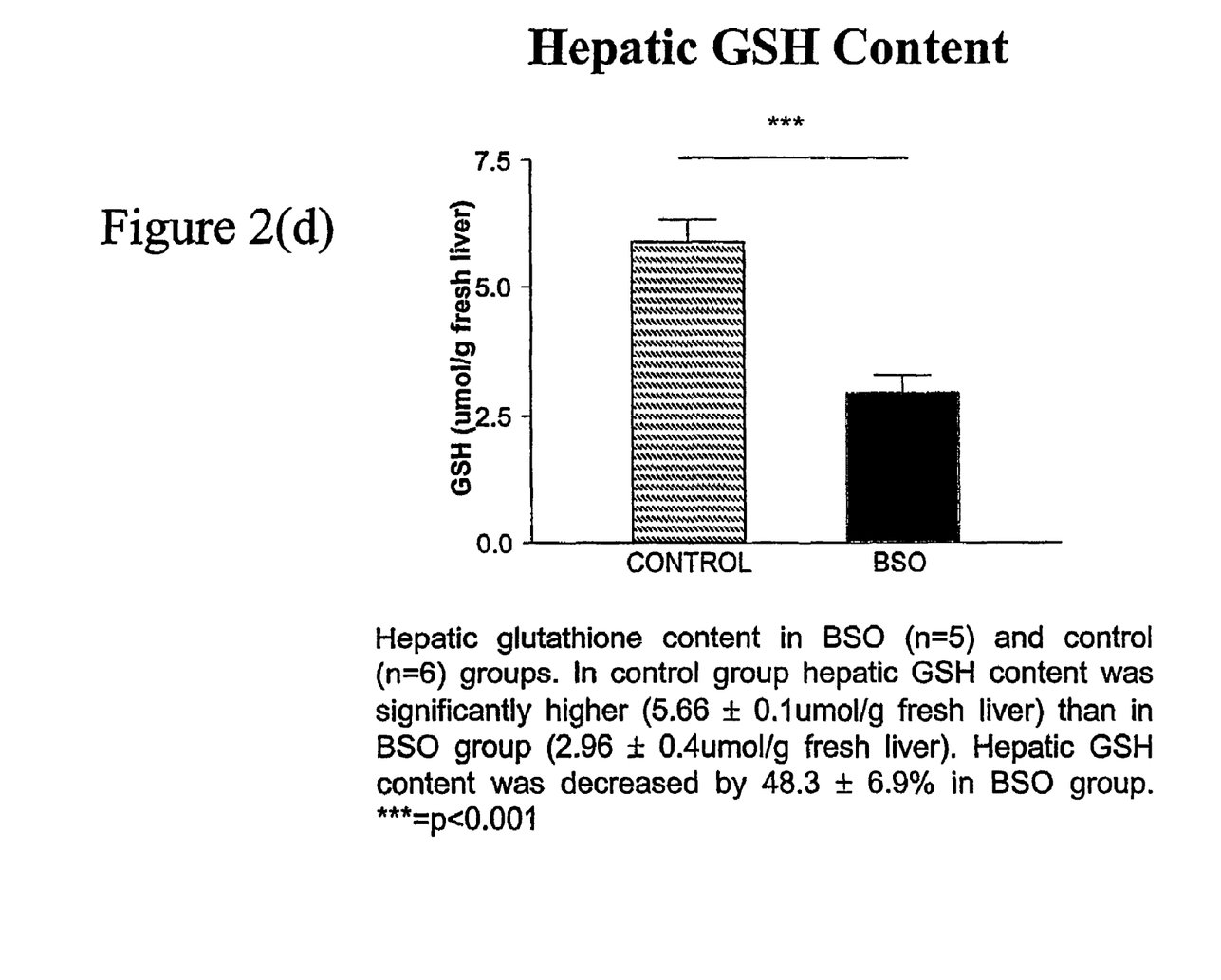

The overall experimental protocol is shown in FIG. 1. Male Wistar rats (8 weeks) were anaesthetized with sodium pentobaribtial (65 mg/kg). Body temperature was maintained at 37±0.5□C. An arterial-venous loop (carotid artery and internal jugular vein) was employed. A catheter was inserted into the portal vein.

RIST (Rapid Insulin Sensitivity Test): Blood samples (25 μl) for arterial glucose analysis were taken from the arterial-venous loop. A stable glucose baseline was established. Insulin (50 mU/kg i.v.) was infused over 5 minutes. Arterial blood samples were taken every 2 minutes. Glucose was adjusted to maintain euglycemia. RIST index=mg glucose/kg infused during RIST.

CONTROL GROUP: Control group (n=6): L-NAME (1 mg/kg i.p.v.) reduces the RIST index from 260.2±15.6 mg glucose/kg to 121.2±12.8 mg glucose/kg (52.3±5.8% inhibition). SIN-1 (5 mg/kg i.p.v.) restores insulin response with a RIST index of 258.1±18.5 mg glucose/kg. ***=p<0.001.

BSO GROUP: BSO group (n=5): The control RIST index was 158.4±12.2 mg glucose/kg. Intraportal administration of L-NAME (1 mg/kg) reduced significantly the RIST index to 109.8±9.1 mg glucose/kg i.p.v. Administration of SIN-1 did not reverse the RIST index to control values. *=p<0.05; ns=non significant.

INSULIN ACTION: HISS-dependent and HISS-independent components of insulin action in BSO and control groups. HISS-independent components are not different in both groups. The direct glucose disposal action of insulin is unaltered by GSH depletion. HISS is significantly reduced in BSO group (49.3±8.56 mg glucose/kg) compared to control group (138.9±22.8 mg glucose/kg) corresponding to a decrease of 64.4% of HISS action. **=p<0.01; ns=non significant.

HEPATIC GSH CONTENT: Hepatic glutathione content in BSO (n=5) and control (n=6) groups. In control group hepatic GSH content was significantly higher (5.66±0.1 μmol/g fresh liver) than in BSO group (2.96±0.4 μmol/g fresh liver). Hepatic GSH content was decreased in 48.3±6.9% in BSO group. ***=p<0.001.

The results are shown in FIG. 2(a-d).

An impaired content of hepatic GSH appears to lead to insulin resistance. The HISS-independent component of insulin action is not altered in the GSH depleted rats. The HISS dependent component of insulin action is decreased significantly in BSO group compared with control group. HISS synthesis/release is dependent on the presence of GSH in the liver.

Example 2

A model of low hepatic GSH and NO production is produced by overnight fasting. Normal hepatic levels of GSH are reduced by an overnight fast. SIN-1 at doses from 2.5 to 10 mg/kg i.p.v. do not reverse fasting induced HDIR but prior administration of glutathione esters raises hepatic GSH levels to those seen in fed animals and restores the ability of the NO donor SIN-1 to serve as the permissive signal that allows insulin to cause HISS release thereby reversing fasting-induced HDIR. GSH administration by itself results in minor reversal of HDIR which only becomes therapeutically significant after the addition of the NO donor.

Thus, there has been provided a method of reducing insulin resistance.

Publications relating to the material described herein include:

Dowell, F. J et al.: *Eur. J. Pharmacol.* 379(23):175-182 (1999); Young, M. E., Leighton, B.: *Biochem. J.* 329:73 (1998); Xie, H., Lautt, W. W.: *Am. J. Physiol.* 270:E858 (1996); Lautt, W. W. et al.: *Can. J. Physiol. Pharmacol.* 76:1 (1998); Sadri, P., Lauft, W. W.: *Am. J. Physiol.* 277:G101 (1999); Modan, M., Halkin, H., Almog, S.: *Journal of Clinical Investigation.* 75:809 (1985); DeMattia, G. et al.: Metabolism 47:993 (1998); Czech, M. P. et al.: *Metabolism.* 27:1987 (1978); Xie, H., Lautt, W. W.: *Am. J. Physiol.* 270:E858 (1996); Sadri, P., Lauft, W. W.: *Am. J. Physiol.* 277:G1 (1999); Khamaisi, M., Kavel, O., Rosenstock, M., Porat, M., Yull, M., Kaiser, N., Rudich A.: *Biochem. J.* 349:579 (2000); Lauft, W. W., Wang, X., Sadri, P., Legare, D., Macedo, M. P.: *Can. J. Physiol. Pharmacol.* 76:1 (1998); Marinho, H. S., Baptista, M., Pinto, R. E.: *Biochem. Biophys. Acta.* 1360:157 (1997); Schrammel, A., Pfeiffer, S., Schmidt, K., Koesling, D., Mayer, B.: *Mol. Pharmacol.* 54:207 (1998).

We claim:

1. A pharmaceutical composition comprising:
   a) a therapeutically effective amount of hepatic glutathione increasing compound for reducing insulin resistance, wherein the hepatic glutathione increasing compound is at least one of N-acetylcysteine, cysteine esters, L-2-oxothiazolidine-4-carboxolate (OTC), gamma glutamylcysteine and its ethyl ester, glutathione ethyl ester, glutathione isopropyl ester, lipoic acid, cystine, cysteine, methionine, or S-adenosylmethionine (SAMe), and
   b) a therapeutically effective amount of hepatic nitric oxide donor for reducing insulin resistance, wherein the hepatic nitric oxide donor is at least one of SIN-1, molsidamine, nitrosylated N-acetylcysteine, nitrosylated cysteine esters, nitrosylated L-2-oxothiazolidine-4-carboxolate (NOTC), nitrosylated gamma glutamylcysteine and its ethyl ester, nitrosylated glutathione ethyl ester, nitrosylated glutathione isopropyl ester, nitrosylated lipoic acid, nitrosylated cysteine, nitrosylated cystine, nitrosylated methionine, or nitrosylated S-adenosylmethionine,
   wherein the hepatic glutathione increasing compound and the hepatic nitric oxide donor are independently bound to albumin or a bile salt.

2. The pharmaceutical composition of claim 1 further comprising a pharmaceutically acceptable antioxidant.

3. A method of reducing insulin resistance in a mammalian patient in need thereof comprising administering the composition of claim 1.

4. The method of claim 3 wherein the patient has lower than normal hepatic glutathione levels.

5. The method of claim 4 wherein the insulin resistance is hepatic insulin sensitizing substance (HISS) dependent insulin resistance (HDIR).

6. The method of claim 4 wherein the hepatic glutathione increasing compound administered causes an increase in hepatic glutathione synthesis.

7. The method of claim 4 wherein the glutathione increasing composition is administered orally.

8. The method of claim 4 wherein the glutathione increasing composition is administered by intravenous injection.

9. The method of claim 4 wherein the nitric oxide donor is SIN-1.

10. The method of claim 4 wherein the hepatic nitric oxide donor is molsidamine.

11. The method of claim 4 further comprising administering a pharmaceutically acceptable anti-oxidant.

12. The method of claim 4 wherein the patient suffers from at least one of non-insulin dependent diabetes, essential hypertension, metabolic obesity, chronic liver disease, fetal alcohol effects, old age and a chronic inflammatory disease.

13. The method of claim 4 wherein the patient is a human.

* * * * *

UNITED STATES PATENT AND TRADEMARK OFFICE
CERTIFICATE OF CORRECTION

PATENT NO. : 7,622,447 B2 Page 1 of 1
APPLICATION NO. : 10/502065
DATED : November 24, 2009
INVENTOR(S) : Lautt et al.

It is certified that error appears in the above-identified patent and that said Letters Patent is hereby corrected as shown below:

Title page, (56) References Cited, Foreign Patent Documents: Delete duplicate reference "WO   WO-00/19992   * 4/2000"

Col. 2, line 1: "skeletal musde uptake," should read --skeletal muscle uptake,--

Signed and Sealed this

Ninth Day of November, 2010

David J. Kappos
*Director of the United States Patent and Trademark Office*